US008272255B2

(12) United States Patent
Halverson et al.

(10) Patent No.: US 8,272,255 B2
(45) Date of Patent: Sep. 25, 2012

(54) SYSTEM AND METHOD FOR PREPARING SAMPLES

(75) Inventors: Kurt J. Halverson, Lake Elmo, MN (US); Stephen C. P. Joseph, Woodbury, MN (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 916 days.

(21) Appl. No.: 12/301,592

(22) PCT Filed: May 22, 2007

(86) PCT No.: PCT/US2007/069460
§ 371 (c)(1),
(2), (4) Date: Nov. 19, 2008

(87) PCT Pub. No.: WO2007/137257
PCT Pub. Date: Nov. 29, 2007

(65) Prior Publication Data
US 2009/0193880 A1    Aug. 6, 2009

Related U.S. Application Data

(63) Continuation-in-part of application No. 11/419,539, filed on May 22, 2006, now abandoned.

(60) Provisional application No. 60/939,236, filed on May 21, 2007.

(51) Int. Cl.
*G01N 1/38* (2006.01)
*G01N 1/14* (2006.01)
*G01N 33/487* (2006.01)
*G01N 1/18* (2006.01)
*G01N 33/02* (2006.01)

(52) U.S. Cl. ... 73/64.56; 73/863; 73/863.23; 73/864.62; 73/864.63; 422/527; 422/534; 422/535; 436/177; 436/179

(58) Field of Classification Search ............... 73/64.56, 73/863, 863.23, 864.62–864.63, 864.51, 73/864.91; 422/527, 534–535, 50, 68.1, 422/82, 939–940, 944, FOR. 103, FOR. 109; 436/177–179
See application file for complete search history.

(56) References Cited

U.S. PATENT DOCUMENTS
3,367,191 A * 2/1968 Richard .................... 73/864.62
(Continued)

FOREIGN PATENT DOCUMENTS
BE    849898    6/1977
(Continued)

OTHER PUBLICATIONS

International Search Report PCT/US2007/064960 Jun. 25, 2009, 3 pgs.
(Continued)

*Primary Examiner* — Thomas P Noland
(74) *Attorney, Agent, or Firm* — Nicole J. Einerson

(57) ABSTRACT

A system and method for preparing samples for analyte testing. The sample preparation system can include a freestanding receptacle. The method can include providing a liquid composition comprising a source and a diluent, and positioning the liquid composition in a reservoir defined by the freestanding receptacle. The method can further include filtering the liquid composition to form a filtrate comprising an analyte of interest, removing at least a portion of the filtrate from the sample preparation system to form a sample, and analyzing the sample for the analyte of interest.

20 Claims, 4 Drawing Sheets

U.S. PATENT DOCUMENTS

| | | | |
|---|---|---|---|
| 3,449,081 A | 6/1969 | Hughes | |
| 3,601,317 A | 8/1971 | Genantonio | |
| 3,748,905 A | 7/1973 | Fletcher et al. | |
| 3,784,039 A | 1/1974 | Marco | |
| 3,819,158 A | 6/1974 | Sharpe et al. | |
| 4,121,306 A * | 10/1978 | Bringman et al. | 600/575 |
| 4,427,406 A * | 1/1984 | Nielsen | 494/16 |
| 4,937,194 A | 6/1990 | Pattillo et al. | |
| 4,984,715 A | 1/1991 | Green | |
| 5,100,801 A | 3/1992 | Ward, Jr. et al. | |
| 5,119,830 A | 6/1992 | Davis | |
| 5,186,897 A | 2/1993 | Eason et al. | |
| 5,291,779 A * | 3/1994 | Govoni et al. | 73/170.17 |
| 5,341,693 A * | 8/1994 | Banu | 73/864.63 X |
| 5,350,080 A | 9/1994 | Brown et al. | |
| 5,385,251 A | 1/1995 | Dunn | |
| 5,403,551 A | 4/1995 | Galloway et al. | |
| 5,569,225 A | 10/1996 | Fleury | |
| 5,617,972 A | 4/1997 | Morano et al. | |
| 5,728,542 A | 3/1998 | Charm et al. | |
| 5,806,711 A | 9/1998 | Morano et al. | |
| 5,833,860 A | 11/1998 | Kopaciewicz et al. | |
| 5,849,505 A | 12/1998 | Guirguis | |
| 6,021,681 A | 2/2000 | Jezek | |
| 6,107,085 A | 8/2000 | Coughlin et al. | |
| 6,180,335 B1 | 1/2001 | Wilkins et al. | |
| 6,221,655 B1 | 4/2001 | Fung et al. | |
| 6,273,600 B1 | 8/2001 | Sharpe et al. | |
| 6,303,363 B1 | 10/2001 | Ward | |
| 6,338,569 B1 | 1/2002 | McGill | |
| 6,458,067 B1 | 10/2002 | Dorin et al. | |
| 6,461,853 B1 | 10/2002 | Zhu | |
| 6,516,953 B1 * | 2/2003 | DiCesare et al. | 210/516 |
| 6,536,687 B1 | 3/2003 | Navis et al. | |
| 6,576,193 B1 | 6/2003 | Cui et al. | |
| 6,588,681 B2 | 7/2003 | Rothrum et al. | |
| 6,595,441 B2 | 7/2003 | Petrie et al. | |
| 6,599,420 B2 | 7/2003 | Sugiyama et al. | |
| 6,669,908 B2 | 12/2003 | Weyker et al. | |
| 6,746,601 B2 * | 6/2004 | Dorin et al. | 210/188 |
| 6,789,945 B2 | 9/2004 | Mobs et al. | |
| 6,820,824 B1 | 11/2004 | Joseph et al. | |
| 6,854,875 B2 | 2/2005 | McGill | |
| 6,955,099 B2 | 10/2005 | Goodin | |
| 7,022,289 B1 | 4/2006 | Schlein et al. | |
| 7,100,461 B2 | 9/2006 | Bradley et al. | |
| 7,108,662 B2 | 9/2006 | Miller et al. | |
| D532,253 S | 11/2006 | White | |
| 7,147,365 B2 | 12/2006 | McGill | |
| 7,168,845 B2 | 1/2007 | McGill | |
| 7,188,785 B2 | 3/2007 | Joseph et al. | |
| 7,211,225 B2 | 5/2007 | Ferguson et al. | |
| 7,223,364 B1 | 5/2007 | Johnston et al. | |
| 7,309,156 B2 | 12/2007 | McGill | |
| 7,374,111 B2 | 5/2008 | Joseph et al. | |
| 7,555,965 B1 * | 7/2009 | Mayeaux | 73/864.62 |
| 2001/0031491 A1 | 10/2001 | Curtis | |
| 2002/0015355 A1 | 2/2002 | Sanpei et al. | |
| 2002/0042145 A1 | 4/2002 | Forsberg | |
| 2002/0085957 A1 * | 7/2002 | Moore et al. | 422/102 |
| 2002/0127307 A1 | 9/2002 | McGill | |
| 2002/0127630 A1 | 9/2002 | DiGuiseppi et al. | |
| 2004/0014237 A1 | 1/2004 | Sugiyama | |
| 2004/0015786 A1 | 1/2004 | Pugliese | |
| 2004/0038425 A1 * | 2/2004 | Ferguson et al. | 436/177 |
| 2004/0114457 A1 | 6/2004 | McGill | |
| 2004/0140373 A1 | 7/2004 | Joseph et al. | |
| 2004/0164182 A1 | 8/2004 | Joseph et al. | |
| 2004/0237674 A1 | 12/2004 | Wu et al. | |
| 2004/0256484 A1 | 12/2004 | Joseph et al. | |
| 2004/0256485 A1 | 12/2004 | Joseph et al. | |
| 2005/0023182 A1 | 2/2005 | Shah | |
| 2005/0112024 A1 | 5/2005 | Guo et al. | |
| 2005/0132775 A1 | 6/2005 | Laughran, Jr. et al. | |
| 2005/0244943 A1 | 11/2005 | Ladisch et al. | |
| 2006/0073538 A1 | 4/2006 | Konrad | |
| 2006/0102550 A1 | 5/2006 | Joseph et al. | |
| 2006/0151630 A1 | 7/2006 | Joseph et al. | |
| 2006/0240458 A1 | 10/2006 | Steichen et al. | |
| 2006/0275798 A1 | 12/2006 | Steichen et al. | |
| 2007/0084736 A1 | 4/2007 | Igota et al. | |
| 2007/0297698 A1 | 12/2007 | Berich | |
| 2008/0054087 A1 | 3/2008 | Joseph et al. | |
| 2008/0268446 A1 | 10/2008 | Steichen et al. | |

FOREIGN PATENT DOCUMENTS

| | | |
|---|---|---|
| EP | 0175326 | 3/1986 |
| EP | 0471947 | 2/1992 |
| EP | 1005909 A2 * | 6/2000 |
| GB | 2298272 A | 8/1996 |
| JP | 61-73054 | 4/1986 |
| JP | 2004-501761 | 1/2004 |
| WO | WO 86/00704 | 1/1986 |
| WO | WO 94/14068 | 6/1994 |
| WO | WO 98/07828 | 2/1998 |
| WO | WO 98/32534 | 7/1998 |
| WO | WO 98/32539 | 7/1998 |
| WO | WO 00/15328 | 3/2000 |
| WO | WO 00/42419 | 7/2000 |
| WO | WO 02/06791 | 1/2002 |
| WO | Wo 03/092573 | 11/2003 |
| WO | WO 2004/031734 | 4/2004 |
| WO | WO 2004/037433 | 5/2004 |
| WO | WO 2004/060574 A1 | 7/2004 |
| WO | WO 2004/060575 A1 | 7/2004 |
| WO | WO 2004/094072 | 11/2004 |
| WO | WO 2004/105949 | 12/2004 |
| WO | WO 2006/037140 | 4/2006 |
| WO | WO 2006/107843 | 10/2006 |
| WO | WO 2007/016691 | 2/2007 |
| WO | WO 2007/062263 | 5/2007 |
| WO | WO 2007/079143 | 7/2007 |
| WO | WO 2007/079188 | 7/2007 |
| WO | WO 2009/067498 | 5/2009 |
| WO | WO 2009/067503 | 5/2009 |
| WO | WO 2009/067513 | 5/2009 |
| WO | WO 2009/067518 | 5/2009 |
| WO | WO 2010/080223 | 7/2010 |

OTHER PUBLICATIONS

Andrews, W. H, et al., "Food Sampling and Preparation of Sample Homogenate," Bacteriological Analytical manual Online, U.S. Food and Drug Admin., Center for Food Safety & Applied Nutrition,[Retrieved from the internet Apr. 7, 2006] pp. 1-10, http://www.cfsan.fda.gov/~ebam/bam-1.html, Apr. 2003.

Andrews, W.H., et al., "Usefullness of the Stomacher in a Microbiological Regulatory Laboratory," Applied and Environmental Microbiology, Jan. 1978, vol. 35, No. 1, pp. 89-93.

Fung, D.Y.C. et al., "The Pulsifier: A New Instrument for Preparing Food Suspensions for Microbiological Analysis," Journal of Rapid Methods and Automation Microbiology 6, Jun. 20, 1997, pp. 43-49.

Ingham, Steven C. et al., "Manual Shaking as an Alternative to Mechanical Stomaching in Preparing Ground Meats for Microbiological analysis," Food Protection Trends, Apr. 2004, vol. 24 No. 4, pp. 253-256.

Sharpe, A.N. et al., "Stomaching : A New Concept in Bactheriological Sample Preparation," Applied Microbiology, Aug. 1972, vol. 24, No. 2, pp. 175-178.

Wu, Vivian, C.H., et al., "Comparison of the Pulsifier and the Stomacher for Recovering Microorganisms in Vegetables," Journal of Rapid Methods and Automation Microbiology 11, Sep. 22, 2003, pp. 145-152, Food & Nutrition Press, Inc., Trumbull, USA.

Sharpe, et al. Ultrasound and Vortex Stirring as Bacteriological Sampling Methods for Foods, Fournal of Applied Bacteriology, 33 (1970), p. 351-357.

* cited by examiner

SYSTEM AND METHOD FOR PREPARING SAMPLES

CROSS REFERENCE TO RELATED APPLICATIONS

This is a national stage filing under 35 U.S.C. §371 of PCT International Patent Application No. PCT/US2007/069460, filed May 22, 2007, which claims the benefit of U.S. Provisional Patent Application No. 60/939,236, filed May 21, 2007 and is a continuation-in-part of U.S. patent application Ser. No. 11/419,539, filed May 22, 2006, the disclosures of which are incorporated herein by reference in their entirety.

BACKGROUND

The present invention relates to a sample preparation system and method, and particularly, to a sample preparation system and method for analyte testing.

Analyzing various food and non-food sources for microorganisms (e.g., bacteria, viruses, fungi, spores) and/or other analytes (e.g., toxins) can be important for public health. Foods grown, purchased and consumed by the general population may contain or acquire microorganisms or other analytes, which can flourish or grow as a function of the environment in which they are located. This growth may lead to accelerated spoilage of the food product or to the proliferation of pathogenic organisms, which may produce toxins or allergens.

Perishable items with a shelf life can be of particular relevance for qualitative or quantitative monitoring of analytes. A convenient and efficient means to remove analytes from a source for analysis can be important in determining product shelf life and safety for human and animal consumption. Some existing systems have been designed to release analytes from food sources. A blender to homogenize samples at 10,000 to 12,000 rpm has been recommended by the Food and Drug Administration, "Food Sampling and Preparation of Sample Homogenate", Chapter 1; FDA Bacteriological Manual, 8$^{th}$ Ed.; 1998, section 1.06. U.S. Pat. No. 3,819,158 (Sharpe et al.) describes a "stomaching" device, which mixes a source and diluents in a bag through the use of two paddles in a kneading-type action. An oscillating device known as the PULSIFIER® is described in U.S. Pat. No. 6,273,600 (Sharpe), which employs a bag placed inside an agitating metal ring. Another technique, vortexing for analyte suspension, has been described in U.S. Pat. No. 6,273,600 (Sharpe).

SUMMARY

Some existing sample preparation methods and devices present inconsistent and sometimes undesirable results. The blender system can homogenize the sample, but can also create a large amount of particulate debris, such that the container needs to be cleaned and sterilized prior to subsequent use. The stomaching device and PULSIFIER® system use plastic bags, which are disposable, but can be cumbersome to handle. The bags are flexible, and therefore, not freestanding when removed from the mixing devices. Removal of samples of liquid compositions (or filtrates) from the bottom of the bags can often be difficult due to possible contamination of a pipette in contact with the sides of the bag. Additionally, samples containing hard objects may pierce the bag and create leaks and sample contamination. In addition, some existing systems also require a separate means for preparing, and subsequently testing, individual samples. Furthermore, some existing systems require extensive cleaning and sterilization between samples, which can be tedious, time-consuming and costly.

Some embodiments of the present invention provide a method for preparing samples for analyte testing. The method can include providing a liquid composition comprising a source and a diluent, and providing a sample preparation system comprising a freestanding receptacle. The method can further include positioning the liquid composition in a reservoir defined by the freestanding receptacle, and filtering the liquid composition to form a filtrate comprising an analyte of interest. The method can further include removing at least a portion of the filtrate from the sample preparation system to form a sample, and analyzing the sample for the analyte of interest.

In some embodiments, a method for preparing samples for analyte testing is provided. The method can include providing a liquid composition comprising a source and a diluent, and providing a sample preparation system comprising a deformable freestanding liner, a freestanding container that is more rigid than the deformable freestanding liner, and a lid. The method can further include positioning the liquid composition in a reservoir defined by the deformable freestanding liner, and coupling the lid to the deformable freestanding liner. The method can further include positioning the deformable freestanding liner in the freestanding container, and filtering the liquid composition to form a filtrate comprising an analyte of interest. The method can further include removing at least a portion of the filtrate from the sample preparation system to form a sample, and analyzing the sample for the analyte of interest.

Other features and aspects of the invention will become apparent by consideration of the detailed description and accompanying drawings.

BRIEF DESCRIPTION OF THE DRAWINGS

Exemplary configurations of the sample preparation system of the present invention are shown in the following figures, wherein like numerals represent like elements.

DETAILED DESCRIPTION

Figure 1:
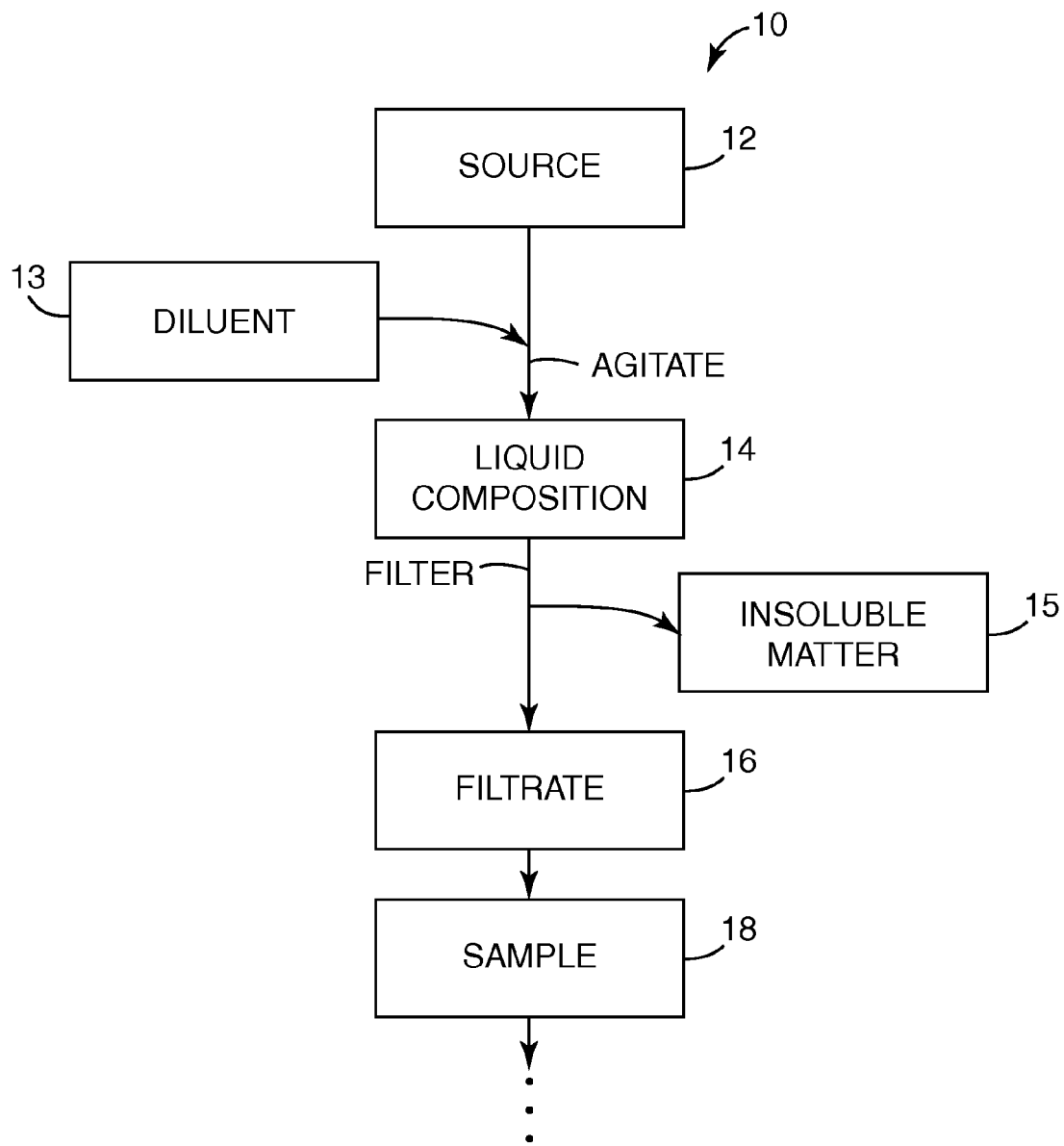
FIG. 1 is a schematic flow chart depicting a sample preparation method according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present invention is generally directed to a system and method for preparing samples. The samples can be further analyzed for the presence or absence of a variety of analytes.

The term "source" is generally used to refer to the food or nonfood desired to be tested for analytes. The source can be a solid, a liquid, a semi-solid, a gelatinous material, and combinations thereof. All or a portion of the source can be used in the sample preparation system and method. When a portion of the source is used, this can sometimes be referred to as a "sample" of the source. However, the term "sample" is generally used herein to refer to the small volume of material that is extracted from the sample preparation system for further analysis (e.g., detection of analytes).

The term "food" is generally used to refer to a solid, liquid or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, cheese, milk, other dairy products (e.g., cheese, yogurt, sour cream), fats, oils, desserts, condiments, spices, pastas, beverages, water, other suitable comestible materials, and combinations thereof.

The term "nonfood" is generally used to refer to sources of interest that do not fall within the definition of "food." Particularly, nonfood sources can include, but are not limited to, substances that are generally not comestible and that may be categorized as one or more of a cell lysate, whole blood or a portion thereof (e.g., serum), other bodily fluids (e.g., saliva, sweat, sebum, urine), feces, cells, tissues, organs, plant materials, wood, soil, sediment, animal feed, medicines, cosmetics, other suitable non-comestible materials, and combinations thereof.

The term "analyte" is generally used to refer to a substance to be detected (e.g., by a laboratory test). A source can be tested for the presence or absence of particular analytes. Such analytes can be present within a source (e.g., on the interior), or exterior (e.g., on the outer surface) of a source. Examples of analytes can include, but are not limited to, microorganisms, biomolecules, chemicals (e.g. pesticides, antibiotics), metal ions (e.g. mercury ions, heavy metal ions), metal-ion-containing complexes (e.g., complexes comprising metal ions and organic ligands), and combinations thereof. A variety of testing methods can be used to identify and/or quantify an analyte, including, but not limited to, microbiological assays, biochemical assays (e.g. immunoassay), or a combination thereof. Specific examples of testing methods that can be used include, but are not limited to, titration, thermal analysis, spectroscopy (e.g., mass spectroscopy, nuclear magnetic resonance (NMR) spectroscopy, Raman spectroscopy, infrared spectroscopy, x-ray spectroscopy, attenuated total reflectance spectroscopy, Fourier transform spectroscopy, gamma-ray spectroscopy, etc.), spectrophotometry (e.g., absorbance, fluorescence, luminescence, etc.), chromatography (e.g., gas chromatography, liquid chromatography, ion-exchange chromatography, affinity chromatography, etc.), electrochemical analysis, growth (e.g., plating (e.g., onto a growth medium, such as agar)), genetic techniques such as polymerase chain reaction (PCR), or other techniques known in the art, such as those that can be conveniently done using Petrifilm™ Plates, and quantified using a Petrifilm™ Plate Reader (3M Company, St. Paul, Minn.), other suitable analyte testing methods, or a combination thereof.

The term "microorganism" is generally used to refer to any microscopic organism, including without limitation, one or more of bacteria (e.g., mobile or vegetative), viruses (e.g., DNA viruses, RNA viruses, enveloped, non-enveloped, etc.), spores, algae, fungi (e.g., yeast), prion, and protozoa. In some cases, the microorganisms of particular interest are those that are pathogenic, and the term "pathogen" is used to refer to any pathogenic microorganism. Examples of pathogens can include, but are not limited to, *Escherichia coli* O157:H7, *Pseudomonas aeruginosa, Salmonella, Listeria monocytogenes, Clostridium botulinun, Staphylococcus aureus, Campylobacter jejuni, Yersinia enterocolitica, Vibrio vulnificus*, and *Enterobacter sakazakii*. Environmental factors that may affect the growth of a microorganism can include pH, moisture content, oxidation-reduction potential, antimicrobial compounds, and biological structures or barriers.

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, protein a polynucleotide, a lipid, a phospholipid, a saccharide, a polysaccharide, and combinations thereof. Specific examples of biomolecules can include, but are not limited to, a metabolite, an allergen (e.g., pollens, dust mites, molds, danders, proteins), a toxin, RNA (e.g., mRNA, total RNA, tRNA, etc.), DNA (e.g., plasmid DNA, plant DNA, etc.), a tagged protein, an antibody, an antigen, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source can include soluble matter (e.g., including the analyte(s) of interest) and insoluble matter (e.g., cell debris). Insoluble matter is sometimes referred to as particulate(s) or debris and can include portions of the source material itself (i.e., from internal portions or external portions (e.g., the outer surface) of the source) or other source residue or debris resulting from an agitation process.

The term "agitate" and derivatives thereof is generally used to describe the process of giving motion to a liquid composition, for example, to mix or blend the contents of such liquid composition. A variety of agitation methods can be used, including, but not limited to, manual shaking, mechanical shaking, ultrasonic vibration, vortex stirring, manual stirring, mechanical stirring (e.g., by a mechanical propeller, a magnetic stirbar, or another agitating aid, such as ball bearings), manual beating, mechanical beating, blending, kneading, and combinations thereof.

The term "filtering" is generally used to describe the process of separating soluble matter and a solvent (e.g., diluent) from insoluble matter. A variety of filtration methods can be used, including, but not limited to, passing the liquid composition through a filter, settling followed by aspiration or decanting, other suitable filtration methods, and combinations thereof. "Settling" is used to refer to allowing the insoluble matter in the liquid composition to settle. Settling may occur by gravity or by centrifugation. The insoluble matter can then be separated from the soluble matter and solvent by aspirating the soluble matter and solvent from the insoluble matter, decanting the soluble matter and solvent, or a combination thereof.

A "filter" is generally used to describe the device used to separate the soluble matter and solvent from the insoluble matter in a liquid composition. Examples of filters can include, but are not limited to, a woven mesh (e.g., a wire mesh, a cloth mesh, a plastic mesh, etc.), a sieve, an ablated film or membrane (e.g., a laser ablated film or membrane, a thermally ablated film or membrane, etc.), a punctured film or membrane, glass wool, a frit, filter paper, etc., and combinations thereof.

The term "filtrate" is generally used to describe the liquid remaining after the insoluble matter has been removed from the liquid composition. Because filtering includes a broad range of methods, the term "filtrate" can also be used to refer to the supernatant that results from allowing insoluble matter in a mixture to settle.

FIG. 1 illustrates a sample preparation method 10 according to one embodiment of the present invention. As shown in FIG. 1, the sample preparation method 10 can begin with obtaining a source 12. A diluent 13 can be combined with all or a portion of the source 12 and agitated to form a liquid composition 14 comprising the source 12 dissolved, dispersed, suspended or emulsified in the diluent 13. As such, the liquid composition 14 is generally a mixture, and can be a solution, an emulsion, a dispersion, a suspension, or a combination thereof.

The source 12, when combined with the diluent 13, can include soluble matter and insoluble matter 15, such that some portions (e.g., the analyte(s) of interest) of the source 12 are dissolved in the diluent 13, while other portions of the source 12 are suspended, dispersed or emulsified in the diluent 13. The liquid composition 14 is then filtered to form a filtrate 16. A sample 18 of the filtrate 16 can then be removed for further analysis.

The diluent 13 is generally a liquid and, in some embodiments, is a sterile liquid. In some embodiments, the diluent 13 can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); nutrients (e.g., that promote selective growth of desired microorganisms); pH buffering agents; enzymes; indicator molecules (e.g. pH or oxidation/reduction indicators); or a combination thereof. In some embodiments, the diluent 13 includes sterile water (e.g., sterile double-distilled water ($ddH_2O$)); one or more organic solvents to selectively dissolve, disperse, suspend, or emulsify the source; aqueous organic solvents, or a combination thereof. In some embodiments, the diluent 13 is a sterile buffered solution (e.g., Butterfield's Buffer, available from Edge Biological, Memphis Tenn.). In some embodiments, the diluent 13 is a selective or semi-selective nutrient formulation, such that the diluent 13 may be used to in the selective or semi-selective growth of the desired analyte(s) (e.g., bacteria). In such embodiments, the diluent 13 can be incubated with the source 12 for a period of time to promote such growth of the desired analyte(s).

In some embodiments, the source 12 includes the diluent 13. For example, a food source that includes a substantial amount of water or other liquid can be mixed without adding additional diluent. In some embodiments, the source 12 may be completely dissolved in the diluent 13, such that the liquid composition 14 includes a minimal amount of insoluble matter 15, making the filtering step unnecessary.

Figure 2:
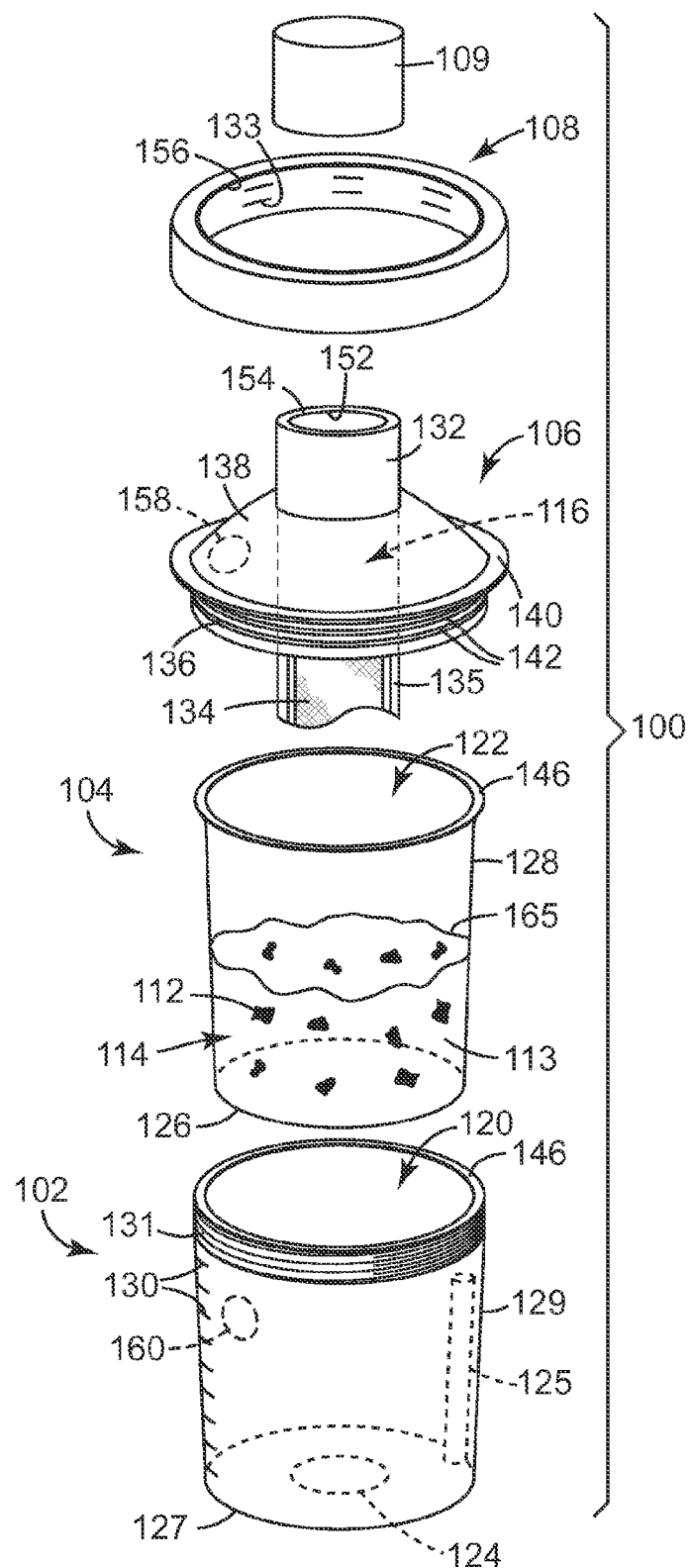
FIG. 2 is an exploded perspective view of a sample preparation system according to one embodiment of the present invention, the sample preparation system including a lid.

FIG. 2 illustrates a sample preparation system 100 according to one embodiment of the present invention. As shown in FIG. 2, the sample preparation system 100 includes a container 102, a liner 104, a lid 106, a collar 108, and a cap 109. In some embodiments, one or more of the components of the sample preparation system 100 are sterile or sterilizable by sterilization and disinfection procedures such as steam, gamma radiation, ethylene oxide, hydrogen peroxide, peracetic acid, hydro-alcoholic solutions, bleach, and combinations thereof. A system having similar features to that of the sample preparation system 100 is described in PCT Publication No. WO 98/32539, U.S. Pat. No. 6,536,687 and U.S. Pat. No. 6,588,681, each of which is incorporated herein in its entirety by reference.

Some embodiments of the present invention employ a plurality of sample preparation systems 100 to allow multiple sample preparation systems 100 be employed in parallel to expedite sample preparation and increase productivity/output. In such embodiments, the plurality of sample preparation systems 100 can be at least partially integrally formed, or they can be separately formed.

In some embodiments, as shown in FIG. 2, the container 102 is freestanding (i.e., self-supporting) and includes a base 127 and a sidewall 129. The container 102 can be formed of a variety of materials including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), high density polypropylene, other suitable polymeric materials capable of forming a self-supporting container, or a combination thereof. The container 102 can be translucent (or even transparent), or opaque, and can be any suitable size, depending on the type, amount and size of source to be analyzed. For example, in some embodiments, the container 102 can have a capacity of 50 mL, 100 mL, 250 mL, or larger.

In some embodiments, as shown in FIG. 2, the sample preparation system 100 includes a liner 104, which is shaped and dimensioned to be received within the container 102. The liner 104 can be disposable (e.g., made for one-time use), to allow the container 102 to be reused without substantial risk for contamination and without extensive cleaning required between uses.

As shown in FIG. 2, the container 102 defines a first reservoir 120, and the liner 104 defines a second reservoir 122. The liner 104 is shaped and dimensioned to be received within the first reservoir 120 of the container 102. In some embodiments, a source 112 and a diluent 113 can be added to the first reservoir 120. In some embodiments, as shown in FIG. 2, the liner 104 is employed, and the source 112 and diluent 113 are positioned within the second reservoir 122, and the liner 104 is positioned within the first reservoir 120. Whether added to the first reservoir 120 or the second reservoir 122, the source 112 and the diluent 113 can be combined (and agitated) to form a liquid composition 114. The liner 104 or the container 102 can serve as a freestanding receptacle that can contain the liquid composition 114.

The source 112 can be added to the container 102 or the liner 104 first, followed by addition of the diluent 113, the diluent 113 can be added first, followed by the source 112, or the source 112 and the diluent 113 can be added simultaneously. Alternatively, the source 112 and diluent 113 can be combined prior to being added to the sample preparation system 100. In some embodiments in which the diluent 113 is added to the container 102 or the liner 104 first, a pre-measured amount of the diluent 113 (e.g., a sterile liquid diluent) can be sealed in the container 102 or the liner 104 with a removably coupled cover, so that the cover can be removed just prior to adding the source 112. Alternatively, in some embodiments, a pre-measured amount of a dry powdered media (e.g., nutrient media) can be sealed in the container 102 or the liner 104 with a removably coupled cover. In such embodiments, the cover can be removed and a solvent (e.g., ddH$_2$O) can be added to form the diluent 113, either prior to or at the same time as the source 112 is added. Alternatively, if the source 112 includes enough of a liquid capable of dissolving the media, the source 112 can be added to the dry powdered media to form the liquid composition 114 that comprises the source 112 and a diluent 113 (e.g., the media dissolved in a solvent provided by the source 112).

The liner 104 can be formed of a variety of materials, including a variety of polymeric materials, including, but not limited to, a polyolefin, including, but not limited to polypropylene (e.g., low density polyethylene (LDPE)), polyethylene, and poly(methylpentene), polyamide (e.g., NYLON®), or a combination thereof. In some embodiments, the liner 104 is formed from a molding process, such as a thermoforming process. The liner 104 can be translucent (or even transparent), or opaque.

In some embodiments, as illustrated in FIG. 2, the liner 104 is freestanding (i.e., self-supporting) and semi-rigid, such that the source 112 and diluent 113 can be loaded into the liner 104 prior to positioning the liner 104 within the container 102, without the liner 104 collapsing or distorting. In addition, a self-supporting liner 104 can aid in weighing, source and diluent addition, transporting, and/or sample removal.

In some embodiments, the liner 104 is self-supporting while also being deformable. The term "deformable" is used to refer to a structure that can be altered from its original shape or state by pressure (e.g., positive or negative) or stress. In embodiments employing a deformable liner 104, pressure can be applied to the liner 104 to reduce its size from its original (i.e., unstressed) dimensions. Such pressure can be used to promote removal of the liquid composition 114 (or a filtrate thereof) from the liner 104.

In some embodiments, as shown in FIG. 2, the container 102 includes an aperture 124 formed in its base 127, through which a user can access the liner 104 to apply pressure to the liner 104 to cause it to deform. Such pressure can be applied directly by hand, or by an additional device, and could be a manual or automated process. The aperture 124 can be shaped and dimensioned according to the desired application of use. In embodiments that do not employ the liner 104, the container 102 need not include the aperture 124.

In some embodiments, the liner 104 includes a relatively rigid base 126 and a relatively thin and deformable sidewall 128, such that when pressure is applied to the base 126 in a direction parallel to the longitudinal axis of the liner 104 (e.g., via the aperture 124 in the container 102), the liner 104 deforms in the longitudinal direction (e.g., by virtue of the sidewall 128 collapsing rather than the base 126). Alternatively, or in addition, the base 126 can be thicker than the sidewall 128. By way of example only, in some embodiments, the thickness of the sidewall 128 is at least 50 μm, in some embodiments, at least 100 μm, in some embodiments, at least 150 μm, and in some embodiments, at least 200 μm. In some embodiments, the thickness of the base 126 is at least 225 μm, in some embodiments, 275 μm, in some embodiments, at least 300 μm, and in some embodiments, at least 350 μm.

The liner 104 can further include one or more of baffles, pleats, corrugations, seams, joints, gussets or a combination thereof, which can assist in controlling the deformability of the liner 104, and/or can further reduce the internal volume of liner 104. In some embodiments, liner 104 does not include any grooves on its internal surface, particularly, at the internal junction between the base 126 and the sidewall 128.

In some embodiments, the liner 104 is deliberately deformed to impart a disruption to the surface geometry of the liner 104. Such a disrupted surface geometry can assist in the breakup of the source 112 during agitation. For example, in some embodiments, an obstruction 125 (e.g., a relatively rigid material) can be positioned between the sidewall 128 of the liner 104 and the container 102 to create a different surface geometry in the sidewall 128 of the liner 104.

As shown in FIG. 2, the container 102 can include indicia 130 to indicate the level (i.e., volume) of contents within the container 102. The indicia 130 can be used to achieve a desired weight ratio of the liquid composition 114, for example, where the weight ratio of the source 112 to the diluent 113 ranges from 1:100 to 1:1. One example of suitable indicia is described in U.S. Pat. No. 6,588,681. Alternatively, or in addition, the liner 104 can include indicia. To enable the use of the indicia 130 on the container 102 and/or the liner 104, the container 102 and/or the liner 104 can be translucent, or even transparent to afford seeing the liquid composition 114 through the sidewall 129 of the container 102 and/or the sidewall 128 of the liner 104. The sidewalls 128 and 129 may also bear other types of markings, such as trademarks, brand names, and the like.

In the embodiment illustrated in FIG. 2, the lid 106 is removably coupled to the liner 104, and the collar 108 is employed to further secure the lid 106 to the container 102. For example, in FIG. 2, the container 102 includes threads 131 at the upper end of the outer surface of the sidewall 129, which are shaped and dimensioned for the collar 108 (having internal threads 133 capable of engaging with the threads 131 on the container 102) to be screwed onto the upper end of the container 102. As an alternative to using the collar 108 for securing the lid 106 to the container 102, other coupling means can be employed including clamping and/or any of the other coupling means described below. In some embodiments, the liner 104 is not employed, and the lid 106 can be coupled directly to the container 102. In such embodiments, the collar 108 need not be employed. Thus, the lid 106 can form a seal, and particularly, a hermetic seal with either the container 102 or the liner 104. In some embodiments, the lid 106 and the container 102 (or the lid 106 and the liner 104) are integrally formed or permanently coupled together.

A variety of coupling means can be employed either between the lid 106 and the liner 104, the lid 106 and the container 102, and/or the collar 108 and the container 102 to allow the respective components to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, other suitable removable coupling means, and combinations thereof. In some embodiments, the sample preparation system 100 need not be reopened after the source 112 and the diluent 113 are added, such that the container 102, the liner 104, the lid 106 and the collar 108 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof.

Figure 3:
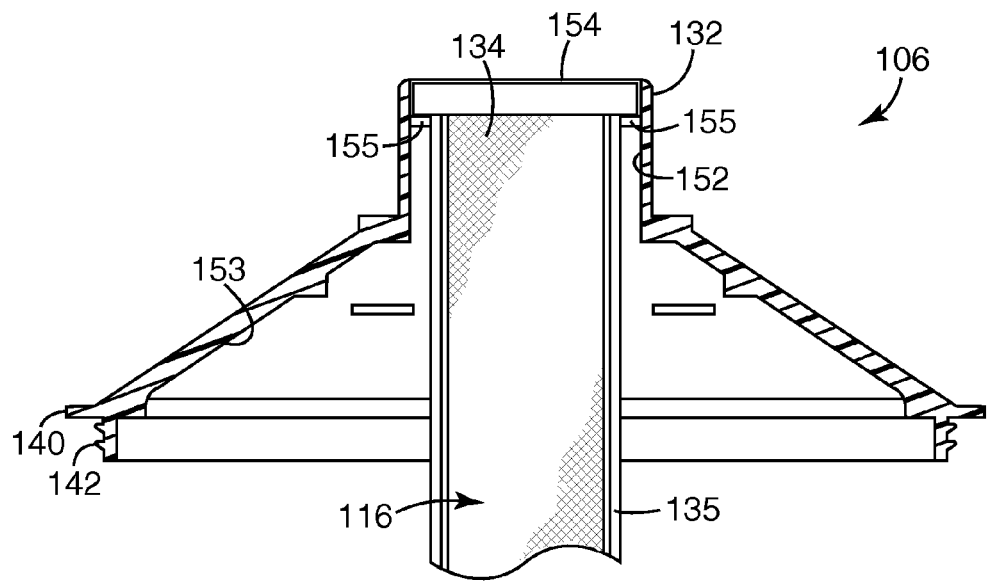
FIG. 3 is close-up cross-sectional view of the lid of FIG. 2.

As shown in FIGS. 2 and 3, the lid 106 further includes a sampling port 132, which can be coupled to a filter 134, a cylindrical portion 136 that is dimensioned to be received within the liner 104, and a generally conical (e.g., frusto-conical) portion 138 that extends from the cylindrical portion 136 to the sampling port 132. At the junction between the cylindrical portion 136 and the conical portion 138, the lid 106 further includes a lip 140 that extends radially outwardly from the cylindrical portion 136 and the conical portion 138.

In some embodiments, the filter is coupled directly to the lid 106. In some embodiments, as shown in FIGS. 2-3, the filter 134 can be supported by a frame 135 and coupled to the lid 106 via the frame 135. The frame 135 can form a portion of the filter 134, the frame 135 can be a part of the lid 106, or the frame 135 can be a separate element that is coupled to both the filter 134 and the lid 106. The frame 135 can be formed of a variety of materials, including, but not limited to, a variety of polymers, metals, ceramics, glasses, and combinations thereof. In the embodiment illustrated in FIGS. 2-3, the filter 134 is formed of a metal mesh, and the frame 135 is formed of a polymer that is bonded to the metal filter 134. The frame 135 is coupled to the lid 106, as described in greater detail below.

The filter 134 and the frame 135 of the embodiment illustrated in FIGS. 2 and 3 are shaped and dimensioned so as to extend below the bottom end of the lid 106, such that when the sample preparation system 100 is assembled, the filter 134 and the frame 135 extend into the second reservoir 122 of the liner 104 (or the first reservoir 120 of the container 102). However, the filter 134 and frame 135 can take on a variety of shapes and sizes. In some embodiments, for example, the frame 135 can include a rigid upper portion (e.g., that is coupled to the lid 106) and a rigid lower portion, and the filter 134 can be coupled therebetween, and the filter 134 can be collapsible.

The cylindrical portion 136 of the lid 106 includes a plurality of circumferential outwardly-projecting protrusions 142 to allow the cylindrical portion 136 to be snap-fit or press-fit to the inner surface of the liner 104. In some embodiments, the inner surface of the liner 104 can include inwardly-projecting protrusions that are used either in lieu of the outwardly-projecting protrusions 142, or in addition to the outwardly-projecting protrusions 142 (e.g., to form a mating relationship therewith).

The liner 104 can include a lip 144 that projects radially outwardly from the sidewall 128 of the liner 104, and which can form an abutting relationship with an upper surface 146 of the container 102 and the lip 140 of the lid 106, such that when the sample preparation system 100 is assembled, the lip 144 of the liner 104 is positioned between the lip 140 of the lid 106 and the upper surface 146 of the container 102, and a seal (e.g., a hermetic seal) is formed. As shown in FIG. 2, the collar 108 includes an inwardly-projecting lip 156, such that when the collar 108 is coupled to the container 102, the lip 156 of the collar 108 presses the lip 140 of the lid 106 into contact with the lip 144 of the liner 104, which is pressed into contact with the upper surface 146 of the container 102 (e.g., to form a higher integrity seal). The above-described means for assembling the sample preparation system 100 and for forming a seal between the components of the sample preparation system 100 are described and illustrated by way of example only. One of ordinary skill in the art will understand, however, that a variety of other mechanisms could be employed to assemble the components of the sample preparation system 100 and to form a seal (e.g., a liquid-tight seal, a hermetic seal, or a combination thereof), such that the sample preparation system 100 is inhibited from leaking under normal operating conditions.

While the lid 106 of the embodiment illustrated in FIGS. 2 and 3 is illustrated as having a generally conical or frusto-conical shape. It should be understood that the lid 106 could have a variety of other shapes, including, but not limited to, a cylindrical shape, a tubular shape having a rectangular or square cross-sectional area, or other shapes suitable to being coupled to the other components of the sample preparation system 100. Similarly, the container 102, the liner 104, and the collar 108 could have a variety of other shapes than the substantially cylindrical shapes illustrated in FIG. 2. In addition, the lid 106 can be dimensioned to accommodate the other components of the sample preparation system 100.

The lid 106 can be formed of a variety of materials, including the materials listed above with respect to the container 102. The lid 106 can be translucent (or even transparent), or opaque, depending on the application of use.

The collar 108 can be formed of a variety of materials, including, but not limited to a variety of polymeric materials, metal materials, and combinations thereof. For example, the collar 108 can be formed of a molded plastic component, or a machined metal (such as aluminum) component. In some embodiments, the collar 108 is formed of a molded plastic component comprising glass fiber reinforced polypropylene.

As shown in FIG. 2, the sampling port 132 of the lid 106 is generally cylindrical and tubular in shape, such that the sampling port 132 defines a portion 152 of the inner surface 153 of the lid 106 and an opening 154 in the lid 106. The lid 106 is hollow and is in fluid communication with the second reservoir 122 when the sample preparation system 100 is assembled. The sampling port 132 does not need to be cylindrical and can instead take on any shaped necessary for a given application. In the embodiment illustrated in FIGS. 2 and 3, the filter 134 is coupled to the sampling port 132 (i.e., via the frame 135) such that the filter 134 is in fluid communication with the lid opening 154, as well as the second reservoir 122.

In the embodiment shown in FIG. 2, the cap 109 is shaped and dimensioned to receive at least a portion of the sampling port 132. As a result, the cap 109 can be coupled to the sampling port 132 of the lid 106 to close the opening in the lid 106 and to seal (e.g., hermetically seal) the sample preparation system 100 from the environment. The cap 109 can be coupled to the lid 106 using any of the above-described coupling means. The cap 109 can be integrally formed with the lid 106 (e.g., a flip-top snap-on cap), or the cap 109 can be separate from the lid 106 (e.g., a screw cap). The cap 109 can be formed of a variety of materials, including the materials listed above with respect to the container 102.

In some embodiments, the lid 106 includes a penetrable membrane or a removable film separating at least a portion of the interior of the lid 106 from the environment, such that the membrane can be pierced or the film removed to access the interior of the lid 106. In such embodiments, the cap 109 need not be employed.

Figure 5:
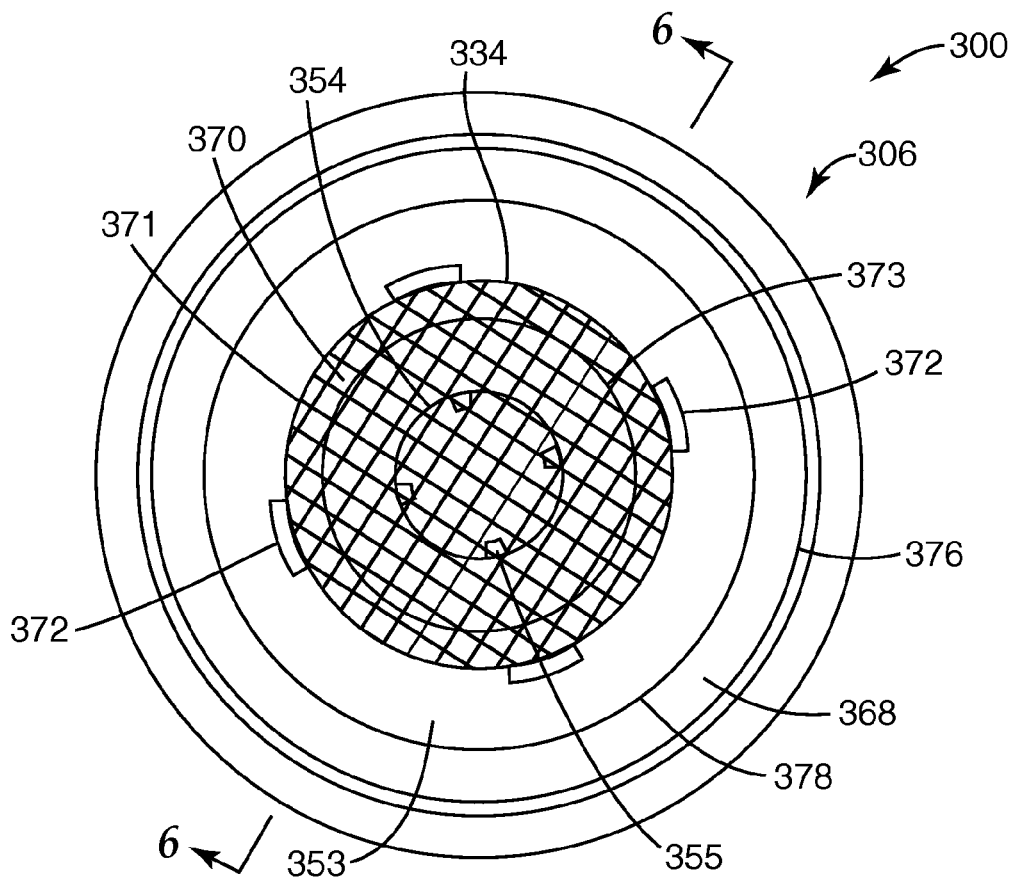
FIG. 5 is a bottom view of a lid of a sample preparation system according to another embodiment of the present invention.
Figure 6:
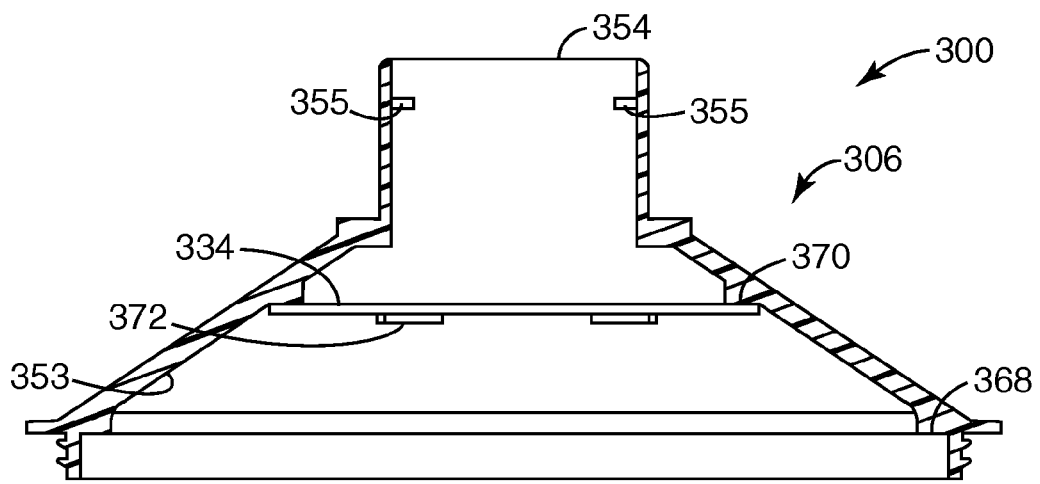
FIG. 6 is a cross-sectional view of the lid of FIG. 5, taken along line 6-6 in FIG. 5.

As shown in FIG. 3, the inner surface 153 of the lid 106 can include a variety of inner circumferential edges to which other components (e.g., additional or alternative filters, the concept of which is illustrated in FIGS. 5-6 and described below) can be coupled. The inner circumferential edges can have any orientation desired, depending on what other components are desired to be coupled to the edges. In some embodiments, the inner circumferential edges are oriented substantially orthogonally to the central longitudinal axis of the lid 106, such that the edges are substantially horizontal in FIG. 3.

In addition, the lid 106 can include a variety of inwardly-extending members to which other components (e.g., filters) can be coupled. For example, as shown in FIG. 3, the filter 134 is supported by the frame 135, and the lid 106 includes inwardly-extending members 155 to which the frame 135 can be coupled via a variety of coupling means, including, but not limited to, any of the coupling means described above. The inwardly-extending members 155 can be integrally formed with the lid 106.

The filter 134 can be of any geometrical shape to sufficiently filter the liquid composition 114. In some embodiments, the filter 134 is deformable and/or collapsible (i.e., such that the filter 134 folds under its own weight). In some embodiments, the filter 134 is rigid and retains its shape (i.e., does not fold under its own weight). The size and number of filters 134 used in a sample preparation system 100, and porosity thereof, may vary, depending on the desired analyte (s) and the insoluble matter in the source 112. By way of example only, in some embodiments, the source 112 comprises food, the desired analyte is bacteria, and the insoluble matter is food particles or debris. In such embodiments, for example, the filter 134 can be selected to retain and/or separate the food particles, while allowing the bacteria to pass through the filter 134 for subsequent analysis. By way of further example, in some embodiments, the source 112 comprises a lysed bacterial cell culture, the desired analyte is one or more of DNA, RNA, a protein, or a metabolite, and the insoluble matter is cellular debris. In such embodiments, for example, the filter 134 can be selected to retain and/or separate the cellular debris, while allowing the desired DNA, RNA, protein, or metabolite to pass through the filter 134 for subsequent analysis.

The filter 134 can have a variety of pore sizes sufficient for retaining particles from the liquid composition 114, while allowing the desired analyte(s) in the liquid composition 114 to pass through the filter 134 for extraction and/or sampling. In some embodiments, the filter 134 has an average pore or mesh size of at least 5 µm, in some embodiments, at least 40 µm, in some embodiments, at least 80 µm, and in some embodiments, at least 120 µm. In some embodiments, the filter 134 has an average pore or mesh size of at most 2000 µm, in some embodiments, at most 1000 µm, in some embodiments, at most 500 µm, and in some embodiments, at most 200 µm.

In the embodiment illustrated in FIGS. 2 and 3, the filter 134 is located in the lid 106, generally in line with the central longitudinal axis of the lid 106. However, in some embodiments, the filter 134 is positioned in an "off-axis" position of the lid 106. For example, an aperture 158 is shown in dashed lines in FIG. 2 to represent a possible "off-axis" position for the filter 134 in the lid 106. An alternative or an additional sampling port can be positioned at the location of the aperture 158 and coupled thereto. The filter 134 can be permanently or removably coupled at one or both locations.

In some embodiments, particularly embodiments that do not employ the liner 104, the filter 134 can alternatively, or additionally, access the interior of the sample preparation system 100 (i.e., the first reservoir 120 of the container 102) via an aperture 160 in the sidewall 129 of the container 102 or the aperture 124 in the base 127 of the container 102 (or an aperture formed in a different location of the base 127 of the container 102). In such embodiments, the filter 134 can be permanently or removably coupled to the sidewall 129 or the base 127 of the container 102. An alternative or additional sampling port can be positioned at the location of the apertures 160 and 124 and coupled thereto. In some embodiments, the sample preparation system 100 can include more than one sampling port, such as the sampling port 132 in the lid 106, an additional sampling port at the location of the aperture 158 in the lid 106, an additional sampling port at the location of the aperture 160 in sidewall 129 of the container 102, and/or an additional sampling port at the location of the aperture 124 in the base 127 of the container 102. The cap 109 or a similar closure device can be used to seal any of the sampling ports at any location on the sample preparation system 100.

Because of the different locations possible for the filter 134, the filter 134 can be shaped and dimensioned to accommodate its position in the sample preparation system 100 and the particular application of use. In any of the possible locations for the filter 134, the filter 134 can be positioned wholly above or wholly below the level 165 of the liquid composition 114, or the filter 134 can be positioned partially above and partially below the level 165 of the liquid composition 114, depending on the type of filtering desired, and how the filter 134 is intended to filter the liquid composition 114. For example, in the embodiment illustrated in FIG. 2, the filter 134 is coupled to the sampling port 132 and, depending on how high the level 165 of the liquid composition 114 is, would typically extend from the sampling port 132 into the interior of the sample preparation system 100, such that the filter 134 is positioned partially above and partially below the level 165 of the liquid composition 114.

The filter 134 is in fluid communication with the interior of the liner 104 and the liquid composition 114 and acts to filter the liquid composition 114 to form a filtrate 116. The filtrate 116 is disposed within the volume of the filter 134 and can be extracted and/or sampled from the adjacent sampling port 132. In embodiments employing filters 134 at multiple locations, the filtrate 116 can be sampled from any of the sampling ports or apertures described above.

The filter 134 can be formed from a variety of materials, including, but not limited to one or more of polypropylene, polyethylene, nylon, polyester, polycarbonate, acrylics such as polymethylmethacrylate, fluorinated polymers (e.g., polytetrafluoroethylene (PTFE)), cellulosics (e.g., modified celluloses such as cellulose acetate), fiberglass, polyurethanes, metals, and combinations thereof. In some embodiments, the filter 134 can be formed of a woven substrate, a nonwoven substrate, a molded structure, can be comprised of other fabrics or fibrous materials, and/or can be formed of a membranous material. The surface area of the filter 134 can be increased by pleating the filter 134, or by other similar techniques.

In some embodiments (no matter which location the filter 134 is in), the filter 134 can be used as a retainer or holder of the source 112. An example of this concept is illustrated in FIG. 4 and described below.

As mentioned above, the liner 104 can be disposable. In addition, in some embodiments, one or more of the lid 106, the cap 109 and the filter 134 can also be disposable. For example, in some embodiments, the lid 106 can be coupled to the liner 104, and the cap 109 and the filter 134 can be coupled to the lid 106. The liner 104, the lid 106, the filter 134 and the cap 109 can form a disposable portion of the sample preparation system 100 that can be used without contaminating the container 102. The disposable portion can be removed from the container 102 and disposed. The container 102 can then be reused with a new liner 104, lid 106, filter 134 and cap 109.

Figure 4:
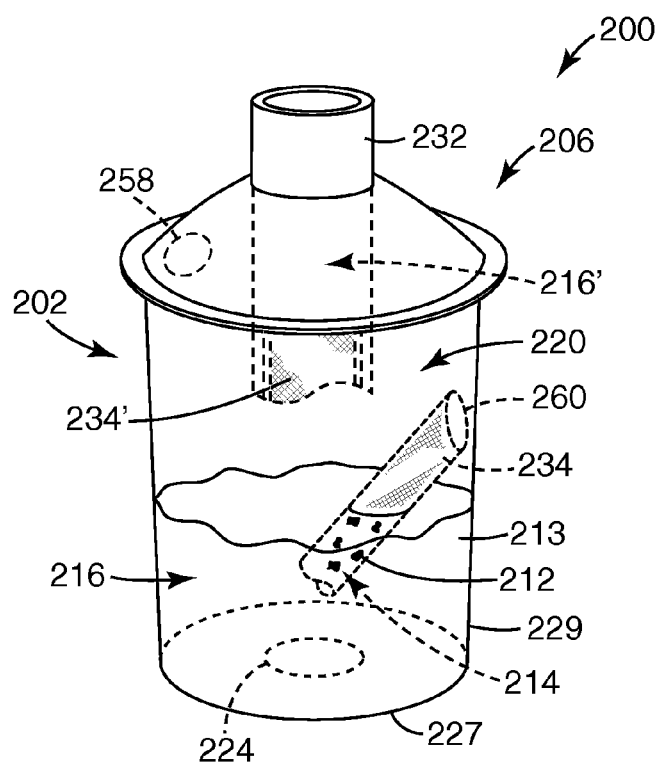
FIG. 4 is a perspective view of a sample preparation system according to another embodiment of the present invention.

FIG. 4 illustrates another sample preparation system 200 according to the present invention, wherein like numerals represent like elements. The sample preparation system 200 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 200 series. Reference is made to the description above accompanying FIGS. 2-3 for a more complete description of the features and elements (and alternatives to such features and elements) of the embodiment illustrated in FIG. 4.

The sample preparation system 200 does not include a liner, and the lid 206 is coupled directly to the container 202. The sample preparation system 200 further includes a filter 234 which is fluidly coupled to an aperture 260 formed in the sidewall 229 of the container 202. Unlike the filter 134 of the sample preparation system 100, the filter 234 functions as a retainer or holder for the source 212.

The filter 234 can be permanently coupled to the container 202 and the source 212 can be added to the filter 234, or the filter 234 can be removably coupled to the container 202, and the source 212 can be added to the filter 234 prior to or after the filter 234 is coupled to the container 202. In some embodiments, the filter 234 can be free-floating within the first reservoir 220 of the container 202, such that the filter 234 contains the source 212 and the diluent 213 is able to flow in and out of the interior of the filter 234 to mix with the source 212.

The source 212 is positioned with the filter 234, and the filter 234 is positioned at least partially below the level of the diluent 213 in the container 202 and is in fluid communication with the interior of the container 202, such that the source 212 can be combined with the diluent 213 to form a liquid composition 214 within the filter 234. The liquid composition 214 positioned within the filter 234 includes the analyte(s) of interest in the diluent 213, as well as any insoluble matter from the source 212. During agitation, the source 212 and the diluent 213 can be mixed to allow the source 212 to be dissolved, dispersed, suspended and/or emulsified in the diluent 213. The diluent 213 and any analyte(s) of interest in the diluent 213 are free to flow in and out of the filter 234, such that the resulting filtrate 216 is positioned outside of the filter 234 and within the reservoir 220 of the container 202, and includes the analyte(s) of interest in the diluent 213.

The filtrate 216 can be sampled from any of a variety of sampling ports or apertures, including the sampling port 232 in the lid 206, the aperture 258 in the lid 206, an additional aperture in the sidewall 229 of the container 202, and/or the aperture 224 in the base 227 of the container 202. In some embodiments, as shown in FIG. 4, one or more of the sampling ports can include an additional filter 234' that functions in the same way as the filter 134 of the sample preparation system 100. In such embodiments, the filtrate 216 is further filtered by the filter 234', and the resulting filtrate 216' is disposed within the filter 234' and can be extracted and/or sampled from the adjacent sampling port (i.e., sampling port 232 in FIG. 4).

The sample preparation system 200 can further include a liner, in which case the diluent 213 and resulting filtrate 216 can be positioned within the liner, provided that sufficient sealing is provided between the liner and the container 202 at the location of the aperture 260.

FIGS. 5-6 illustrate another sample preparation system 300 according to the present invention, wherein like numerals represent like elements. The sample preparation system 300 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 300 series. Reference is made to the description above accompanying FIGS. 2-3 for a more complete description of the features and elements (and alternatives to such features and elements) of the embodiment illustrated in FIGS. 5-6.

FIGS. 5-6 show only the lid 306 of the sample preparation system 300. The other components of the sample preparation system 300 can be assumed to be the same as that of the sample preparation system 100 described above, and thus for clarity, are not shown in FIGS. 5-6.

The lid 306 is substantially similar to the lid 106 described above and illustrated in FIGS. 2-3, except that the lid 306 includes a filter 334 that is substantially planar and coupled to the inner surface 353 of the lid 306. The inner surface 353 of the lid 306 includes an upper inner circumferential edge 370 and a lower inner circumferential edge 368. As shown in FIG. 5, the upper inner circumferential edge 370 includes a downwardly facing surface that extends from an outer circumference 371 to an inner circumference 373. Similarly, the lower inner circumferential edge 368 includes a downwardly facing surface that extends from an outer circumference 376 to an inner circumference 378. The outer periphery of the filter 334 is coupled to the upper inner circumferential edge 370 of the inner surface 353. In addition, the filter 334 is in contact with retaining walls 372. The retaining walls 372 extend downwardly from the inner surface 353 of the lid 106 to retain the outer periphery of the filter 334.

The filter 334 can be coupled to the lid 306 using the same coupling means described above with respect to the lid 106. The filter 334 can be permanently or removably coupled to the lid 306. The degree of coupling between the filter 334 and the lid 306 may vary depending on a number of factors including, but not limited to, the filter 334 material, the lid 306 material, the size and texture of the coupled surface area, and the type of coupling means used. For example, if the filter 334 includes frayed edges, a wider and/or knurled coupling surface area may be used (e.g., the upper inner circumferential edge 370 can be knurled). Such a wider and/or knurled ultrasonic weld may capture frayed edges of the filter 334. To minimize the amount of fraying, the filter 334 can be cut using a laser, which can fuse the edges of the filter 334. Because the resulting laser-cut filter 334 would include a minimum amount of fraying, if any, a narrower coupling area can be used. In some embodiments, the coupling area extends completely around the outer periphery of the filter 334. In some embodiments, the coupling area can have an average width (i.e., a dimension within the same plane and substantially perpendicular to the outer periphery of the filter 334) of up to 5.0 mm, and in some embodiments, ranging from 1.0 mm to 3.0 mm. Alternatively, the filter 334 can be integrally formed with the lid 306, for example, by a molding process.

The filter 334 can be formed of the same material as the lid 306 or a different material. The filter 334 may be flexible, or semi-rigid. In some embodiments, the filter 334 is formed from a nylon nonwoven or woven fabric, while the lid 306 is an injection molded part formed from polypropylene. In such embodiments, the nylon filter 334 can be coupled to the lid 306 via an ultrasonic welding technique. During ultrasonic welding, at least a portion of the upper inner circumferential edge 370 can melt to mechanically bond the filter 334. Since nylon has a higher melting temperature than polypropylene, the nylon filter 334 can maintain its structural integrity during the ultrasonic welding process. In such embodiments, at least a portion of the upper inner circumferential edge 370 can enter into a portion of filter 334, thereby encapsulating a portion of the filter 334.

The filter 334 can have dimensions and shapes that vary for a given application. The filter 334 can have any desired shape including, but not limited to, a circular shape, a square shape, a rectangular shape, a triangular shape, a polygonal shape, a star shape, other suitable shapes, and combinations thereof. In the embodiment illustrated in FIGS. 5 and 6, the filter 334 has a substantially circular shape.

The dimensions of the filter 334 may vary depending on the size of the lid 306. In some embodiments, the filter 334 has a largest dimension (i.e., length, width, or diameter) ranging from 15 mm to 100 mm, although the filter 334 may have smaller or larger dimensions. For example, in some embodiments, the filter 334 can have a circular shape and a diameter of 56 mm.

With continued reference to FIGS. 5 and 6, the retaining walls 372 can be integrally formed with the lid 306. In some embodiments, as shown in FIG. 5, the lid 306 comprises two or more retaining walls 372, wherein (i) each retaining wall 372 has a circumferential length greater than its thickness, (ii) each retaining wall 372 is positioned along an outer periphery of the filter 334, and (iii) the total circumferential length of the two or more retaining walls 372 is less than the total circumferential length of the outer periphery of the filter 334.

As shown in FIG. 5, the lid 306 includes four retaining walls 372 equally spaced from one another along outer circumference 371 of the upper inner circumferential edge 370. In some embodiments, each retaining wall 372 has a thickness ranging from 800 µm to 1200 µm, a length (i.e., in this exemplary embodiment, an arc length) extending a distance ranging from 1.0 mm to 22.0 mm along outer circumference 371, and a height ranging from 1.0 mm to 5.0 mm. In some embodiments, each retaining wall 372 has a segmented configuration so as to not inhibit (or minimize the effect on) fluid flow around the retaining wall 372.

The lid 306 includes an opening 354 and inwardly-extending members 355. The inwardly-extending members 355 can be used to couple an additional filter (not shown) to the lid 306 in the same way that the filter 134 is coupled to the lid 106 in FIGS. 2 and 3. In such embodiments, the filter 334 is located below the additional filter, and the additional filter can have a length dimension less than the distance from the top the lid 306 to the filter 334.

In some embodiments, as shown in FIGS. 5 and 6, the filter element 334 has a total surface area that is greater than a smallest cross-sectional area of the lid 306. In the lid 306, the smallest cross-sectional area is the cross-sectional area of lid opening 354. In some embodiments, more than one filter is coupled to the lid 306 in a similar manner as the filter 334. For example, in some embodiments, the filter 334 or an additional filter (not shown) can be coupled to the lower inner circumferential edge 368. That is, one or more filters 334 can be coupled to the lid 306 and positioned anywhere along the inner surface 353 of the lid 306. In embodiments employing more than one filter 334, the filters 334 can be similar to one another or different from one another. That is, the filters 334 can be formed of the same or different materials, and the filters 334 can have the same or sequentially smaller pore sizes.

As an example, a first filter 334 can be coupled to the upper inner circumferential edge 370 and can have a diameter of 56 mm, an element pore size of 80 µm, and can be at least partially surrounded by one or more retaining walls 372, while a second filter 334 can be coupled to the lower inner circumferential edge 368 and can have a diameter of 96 mm, an element pore size of 200 µm, and can be at least partially surrounded by the inner surface 353 of the lid 306.

Any of the above-described filters 134, 234 and 334 can be used in combination with one another in one sample preparation system. For example, as described above, the filter 134 can be used in combination with the filter 234 and/or the filter 334, to provide a series of filters for different applications, and/or for the removal of successively smaller particulates from the liquid composition.

Alternatively, or in addition, more than one of each type of filter 134, 234 or 334 can be employed (and in some embodiments, can be nested) for the removal of successively smaller particulates from the liquid composition. For example, the filters may be arranged where a coarse filter acts as a pre-filter with a larger pore size relative to subsequent filters, which have successively smaller pore sizes for the collection of a filtrate. The filters may be arranged for use of the sample preparation system in an upright position, and/or the filters may be arranged for use of the sample preparation system when it is inverted.

Any of the sample preparation systems 100, 200, 300 described herein can be used to prepare samples by generally following the sample preparation method 10 described above and illustrated in FIG. 1. An exemplary method will now be described in detail using the sample preparation system 100 of FIGS. 2 and 3.

A source 112 and a diluent 113 can be added to the first reservoir 120 of the container 102 and combined to form a liquid composition 114. As mentioned above, the liner 104 or the container 102 can serve as a freestanding receptacle that can contain the liquid composition 114. The lid 106 can be coupled to the liner 104 prior to or after the liner 104 is positioned within the container 102. The collar 108 can be coupled to the container 102 to secure the components together, and the lid opening 154 can be closed using the cap 109.

The sample preparation system 100 can be agitated to mix the source 112 and the diluent 113 and to dissolve, disperse, suspend and/or emulsify the source 112 in the diluent 113. Agitation may be in a circular orbit, an elliptical orbit, a random orbit, a combination thereof, or of other means to ensure effective and efficient mixing of the source 112 and the diluent 113. The sample preparation system 100 may be secured by clamping or other means during agitation to minimize spillage and/or loss of the liquid composition 114.

In some embodiments, the liquid composition 114 in the sample preparation system 100 can be agitated by a Burell Model 75 Wrist Action Shaker (Burrell Scientific, Pittsburgh, Pa.), at a frequency of 10 to 2000 cycles/minute, and in some embodiments, at a frequency of 200 to 500 cycles/minute for a selected duration of time. In some embodiments, the sample preparation system 100 can be mounted at a distance from the shaker arm from between 5 cm and 50 cm, and in some embodiments, between 10 cm and 20 cm. In some embodiments, the sample preparation system 100 can inscribe an arc of 5 degrees to 30 degrees, and in some embodiments, between 15 degrees and 20 degrees. The liquid composition 114 may be agitated for at least 10 seconds, in some embodiments, at least 15 seconds, in some embodiments, at least 30 seconds, in some embodiments, at least 40 seconds, and in some embodiments, at least 60 seconds. In some embodiments, the liquid composition 114 can be agitated for at most 15 minutes, in some embodiments, at most 10 minutes, in some embodiments, at most 5 minutes, and in some embodiments, at most 3 minutes.

In some embodiments, the liquid composition 114 can be vortexed in a VX-2500 Multi-Tube Vortexer (VWR Scientific Products, West Chester, Pa.) at an agitation frequency of 200 to 5000 rpm, and in some embodiments, of 1000 to 3000 rpm for a selected duration of time. The vortex orbit can be circular, elliptical, random, or a combination thereof. In some embodiments, the orbit is between 0.25 cm and 5 cm, and in some embodiments, between 1 cm and 3 cm.

As mentioned above, an array or plurality of sample preparation systems 100, 200 and/or 300 can be agitated simultaneously, by being placed on a plate, an arm or other device, and secured by gravity, clamping or other means for subsequent agitation. For example, in some embodiments, 1 to about 50 sample preparation systems 100, 200 and/or 300 are agitated simultaneously, and in some embodiments, about 10 to about 25 sample preparation systems 100, 200 and/or 300 are agitated simultaneously on a single agitation device or with multiple agitation devices.

In some embodiments, the liquid composition 114 can be agitated by the addition of a mechanical stirrer having a shaft and stirring blades, which may be inserted through the lid opening 154 (e.g., when no filter 134 is present), or alternatively, through any of the other possible apertures. Agitation of the liquid composition 114 may be further accomplished with steel ball bearings, magnetic stirring bars, blades, and other means to assist in breaking up and/or dispersing the source 112 in the diluent 113 to release the analyte(s) of interest from the source 112. The agitation methods described above are included by way of example only and are not intended to be limiting. One of ordinary skill in the art will understand that other similar agitation methods can be employed.

The liquid composition 114 can be filtered using the filter 134 to form a filtrate 116 positioned within the filter 134 that includes the diluent 113 and any analyte(s) of interest in the diluent 113. All or a portion (e.g., a sample) of the filtrate 116 can be removed from the interior of the filter 134 for further analysis.

In some embodiments, the level 165 of the liquid composition 114 is high enough that the filter 134 is positioned partially above and partially below the level 165 of the liquid composition 114. The sample preparation system 100 can be positioned upright, tipped, tilted or inverted to adjust the level 165 of the liquid composition 114 as necessary. In such embodiments, the interior of the filter 134 can be accessed via the lid opening 154, and a sample of the filtrate 116 can be removed via aspiration (e.g., by pipetting) from the interior of the filter 134. Alternatively, the filtrate 116 can be removed by decanting the filtrate 116 from the lid opening 154, and/or the liner 104 can be deformed and the filtrate 116 forced from the lid opening 154 by applying pressure to the liner 104 (e.g., to the base 126 of the liner 104 via the aperture 124 in the base 127 of the container 102).

In some embodiments, the level 165 of the liquid composition 114 is below the bottom of the filter 134, such that the filter 134 is positioned wholly above the level 165 of the liquid composition 114. In such embodiments, the sample preparation system 100 can be inverted to cause the liquid composition 114 to be filtered by the filter 134, such that the filtrate 116 is located within the filter 134. Pressure can be applied to the liner 104 as described above to force the filtrate 116 into the interior of the filter 134, and/or from the lid opening 154. Alternatively, the filter 134 can be configured such that when the sample preparation system 100 is returned to an upright position after inversion, the filter 134 retains a filtrate 116 in its interior that can be removed by aspiration and/or decanting.

As described above, in some embodiments, such as the sample preparation system 200 illustrated in FIG. 4, the filter 234 can act as a retainer or holder for the source 212. In such embodiments, a diluent 213 can be added to the first reservoir 220 of the container 202 (or the container 202 can be pre-filled with a pre-measured amount of diluent 213), and the source 212 can be positioned within the filter 234. The lid 206 can be coupled to the container 202, and the sample preparation system 200 can be closed using a cap or similar closure device. The assembled and closed sample preparation system 200 can be agitated to allow the diluent 213 to flow into and out of the filter 234, such that the liquid composition 214 is located within the filter 234, and the filtrate 216 is located outside of the filter 234 and within the first reservoir 220 of the container 202.

As mentioned above, the filtrate 216 can be removed from any of a variety of sampling ports (e.g., the sampling port 232), and can be further filtered to removed additional particulates that may still be present in the filtrate 216. For example, the filtrate 216 can be further filtered by a filter 234' having a smaller pore size than that of the filter 234 coupled to the sidewall 229 of the container 202, such that a second filtrate 216' is formed within the filter 234'. The second filtrate 216', or a sample thereof, can be removed using any of the above-described techniques.

The following working examples are intended to be illustrative of the present invention and not limiting.

EXAMPLES

All solvents and reagents were obtained from Aldrich Chemical Company, Milwaukee, Wis., unless otherwise noted. All percents and amounts are by weight unless otherwise specified. 3M™ Company Paint Preparation System liners (part number 16114) and freestanding containers (part number 16115) and associated lids and collars were supplied by 3M Company of St. Paul, Minn. The shaker used was Burrell model 75-wrist action shaker supplied by Burrell Scientific Company of Pittsburgh, Pa. Sterile diluent (Butterfield's buffer) was purchased from Edge Biological of Memphis, Tenn. The vortexer was a model VX-2500 Multi-Tube Vortexer from VWR Scientific Products of West Chester, Pa. Aerobic count was determined using 3M™ Petrifilm™ Aerobic Count Plates and Plate Readers were obtained from 3M Company of St. Paul, Minn.

Ground beef and pork (estimated to contain 25% fat) samples were purchased from local grocery stores. Portions (150 grams) were separated, placed in plastic bags, and stored in a freezer at −20° C. Spinach leaves were also purchased from local grocery stores, and stored at 4° C. in their original containers. Prior to use, required portions of ground beef and pork were removed from the freezer, kept for approximately 2 hours at room temperature (i.e., 25° C. to thaw the samples, followed by thorough mixing in the bag using a wooden spatula before use. Spinach samples were tested immediately after removal from the 4° C. storage.

Comparative Example 1 (C1)

This example demonstrates quantification of analytes released from a ground beef sample using the stomaching procedure. A portion of ground beef (11 g) was placed inside the filter of a filtered stomacher bag (Seward STOMACHER® laboratory blender, Model 400 filter bag from Seward, Inc. of Norfolk, UK), and after addition of Butterfield's buffer (99 mL), the bag was placed in a STOMACHER® laboratory blender (Model 400, from Seward, Inc., of Norfolk, UK). The liquid composition was stomached at 230 rpm for the designated times as reported in Table 1. A filtrate was formed in the volume between the filter and the bag wall. After each time interval, 2 mL of the filtrate was collected by pipette from the space between the outside of the filter and the bag wall and transferred to a sterile test tube. A portion of the collected filtrates (500 µL) was diluted with Butterfield's Buffer (99 mL), and shaken manually for approximately 10 seconds after which an aerobic count for each filtrate was determined and reported in Table 1.

Comparative Example 2 (C2)

This example demonstrates quantification of analytes released from a ground pork sample using the stomaching procedure. A portion of ground pork (11 g) was placed inside the filter of a filtered stomacher bag (Seward STOMACHER® laboratory blender, Model 400 filter bag from Seward, Inc. of Norfolk, UK), and after addition of Butterfield's buffer (99 mL), the bag was placed in a STOMACHER® laboratory blender (Model 400, from Seward, Inc., of Norfolk, UK). The liquid composition was stomached at 230 rpm for the designated times as reported in Table 1. A filtrate was formed in the volume between the filter and the bag wall. After each time interval, 2 mL of the filtrate was collected by pipette from the space between the outside of the filter and the bag wall and transferred to a sterile test tube. A portion of the filtrates collected (1000 µL) was diluted with Butterfield's Buffer (9 mL), and shaken manually for approximately 10 seconds after which an aerobic count for each filtrate was determined and reported in Table 1.

Comparative Example 3 (C3)

This example demonstrates quantification of analytes released from spinach leaves using the stomaching procedure. A portion of spinach leaves (11 g) was placed inside the filter of a filtered stomacher bag (Seward STOMACHER® laboratory blender, Model 400 filter bag from Seward, Inc. of Norfolk, UK), and after addition of Butterfield's buffer (99 mL), the bag was placed in a STOMACHER® laboratory blender (Model 400, from Seward, Inc., of Norfolk, UK). The liquid composition was stomached at 230 rpm for the designated times as reported in Table 1. A filtrate was formed in the volume between the filter and the bag wall. After each time interval, 2 mL of the filtrate was collected by pipette from the space between the outside of the filter and the bag wall and transferred to a sterile test tube. A portion of the filtrates collected (1000 µL) was serially diluted with Butterfield's Buffer to a final concentration of 1:20,000, after which an aerobic count for each filtrate was determined and reported in Table 1.

Example 1 (E1)

This example demonstrates quantification of analytes released from a ground beef sample using mechanical shaking and a sample preparation system of the present disclosure. An empty liner was placed on a balance and ground beef (11 g), which served as the source, was transferred into the liner. The liner was then removed from the balance and placed in a container. Sterile diluent (99 mL) was added to the liner containing the ground beef source, and a lid was coupled to the liner and container. The lid comprised a filter in the form of the filter 134 of FIGS. 2 and 3. A threaded collar was then screwed onto the container to secure the sample preparation system in an assembled state. An opening in the lid was sealed with a separate cap. The sample preparation system containing a liquid composition comprising the ground beef and diluent was placed in a clamp secured to an arm of a shaker. The distance from the center of the sample preparation system to the rod on the shaker was approximately 20 cm. The sample was shaken for 15 seconds at an equipment dial setting of 10, corresponding to a frequency of approximately 6 cycles per second at an approximate arc of 17 degrees. After this time period, with the cap removed, approximately 2 mL of the liquid composition was decanted through the filter in the lid (i.e., as a filtrate) into a sterile test tube. The sample preparation system was capped, returned to the shaking device, and agitated for additional time periods as required. The mixing/decanting cycle was repeated as described, and filtrates were collected at 60, 120, and 240 seconds time points. A portion of filtrates collected (500 µL) was diluted with Butterfield's Buffer (99 mL), and shaken manually for approximately 10 seconds after which an aerobic count for each filtrate was determined and reported in Table 1.

Example 2 (E2)

This example demonstrates quantification of analytes released from a ground beef sample using a vortex mixer and a sample preparation system of the present disclosure. An empty liner was placed on a balance and ground beef (11 g), which served as the source, was transferred into the liner. The liner was then removed from the balance and placed in a container. Sterile diluent (99 mL) was added to the liner containing the ground beef source and a lid was coupled to the liner and container. The lid comprised a filter in the form of the filter 134 of FIGS. 2 and 3. A threaded collar was then screwed onto the container to secure the sample preparation system in an assembled state. An opening in the lid was sealed with a separate cap. The sample preparation system containing a liquid composition comprising the ground beef and diluent was placed and secured on the platform of the Vortexer with an eccentric orbit (approximately 6 mm×4 mm). The liquid composition was mixed for 15 seconds at an equipment dial setting of 10, corresponding to rotation speed of approximately 2500 rpm. After this time period, the cap was removed and approximately 2 mL of the liquid composition was decanted through the filter in the lid (i.e., as a filtrate) into a sterile test tube. The sample preparation system was capped, returned to the vortexing device, and mixed for additional time periods as required. The mixing/decanting cycle was repeated as described and filtrates were collected at 60, 120, and 240 seconds time points. A portion of the filtrates collected (500 µL) was diluted with Butterfield's Buffer (99 mL) and shaken manually for approximately 10 seconds after which an aerobic count for each filtrate was determined and reported in Table 1.

Example 3 (E3)

This example demonstrates quantification of analytes from a ground pork sample using a vortex mixer and a sample preparation system of the present disclosure. An empty liner was placed on a balance and ground beef (11 g), which served as the source, was transferred into the liner. The liner was then removed from the balance and placed in a container. Sterile diluent (99 mL) was added to the liner containing the ground pork source and a lid was coupled to the liner and container. The lid comprised a filter in the form of the filter 134 of FIGS. 2 and 3. A threaded collar was then screwed onto the container to secure the sample preparation system in an assembled state. An opening in the lid was sealed with a separate cap.

The sample preparation system containing a liquid composition comprising ground pork and diluent was placed, and secured on the platform of the Vortexer with an eccentric orbit (approximately 6 mm×4 mm). The liquid composition was mixed for 15 seconds at an equipment dial setting of 10, corresponding to a rotation speed of approximately 2500 rpm. After this time period, the cap was removed and approximately 2 mL of the liquid composition was decanted through the filter in the lid (i.e., as a filtrate) into a sterile test tube. The sample preparation system was capped, returned to the vortexing device, and mixed for additional time periods as required. The mixing/decanting cycle was repeated as described and filtrates were collected at 60, 120, and 240 seconds time points. A portion of the filtrates collected (1000 μL) was diluted with Butterfield's Buffer and shaken manually for approximately 10 seconds after which an aerobic count for each filtrate was determined and reported in Table 1.

Example 4 (E4)

This example demonstrates quantification of analytes released from spinach leaf samples using a mechanical shaker and a sample preparation system of the present disclosure. An empty liner was placed on a balance and a spinach leaf (11 g), which served as the source, was transferred into the liner. The liner was then removed from the balance and placed in a container. Sterile diluent (99 mL) was added to the liner containing the spinach leaf source, and a lid was coupled to the liner and container. The lid comprised a filter in the form of the filter 134 of FIGS. 2 and 3. A threaded collar was then screwed onto the container to secure the sample preparation system in an assembled state. An opening in the lid was sealed with a separate cap. The sample preparation system containing a liquid composition comprising the spinach leaf and diluent was placed in a clamp secured to the arm of the shaker. The distance from the center of the sample preparation system to the rod on the shaker was approximately 20 cm. The liquid composition was shaken for 15 seconds at an equipment dial setting of 10, corresponding to a frequency of approximately 6 cycles per second at an approximate arc of 17 degrees. After this time period, with the cap removed, approximately 2 mL of liquid composition was decanted through the filter in the lid (i.e., as a filtrate) into a sterile test tube. The sample preparation system was capped, returned to the shaking device, and agitated for additional time periods as required. The mixing/decanting cycle was repeated as described and filtrates were collected at 60, 120, and 240 seconds time points. A portion of the filtrates collected (1000 μL) was serially diluted with Butterfield's Buffer to a final concentration of 1:20,000 after which an aerobic count for each filtrate was determined and reported in Table 1.

Example 5 (E5)

This example demonstrates quantification of analytes released from a spinach leaf source using a vortex mixer and a sample preparation system of the present disclosure. An empty liner was placed on a balance and a spinach leaf (11 g) was transferred into the liner. The liner was then removed from the balance and placed in a container. Sterile diluent (99 mL) was added to the liner containing the spinach leaf source, and a lid was coupled to the liner and container. The lid comprised a filter in the form of the filter 134 of FIGS. 2 and 3. A threaded collar was then screwed onto the container to secure the sample preparation system in an assembled state. An opening in the lid was sealed with a separate cap. The sample preparation system containing a liquid composition comprising the spinach leaf and diluent was placed and secured on the platform of the Vortexer with an eccentric orbit (approximately 6 mm×4 mm). The liquid composition was mixed for 15 seconds at an equipment dial setting of 10, corresponding to rotation speed of approximately 2500 rpm. After this time period, with the cap removed, approximately 2 mL of the liquid composition was decanted through the filter in the lid (i.e., as a filtrate) into a sterile test tube. The sample preparation system was capped, returned to the vortexing device, and mixed for additional time periods as required. The mixing/decanting cycle was repeated as described and filtrates were collected at 60, 120, and 240 seconds time points. A portion of filtrates collected (1000 μL) was serially diluted with Butterfield's Buffer to a final concentration of 1:20,000, after which an aerobic count for each filtrate was determined and reported in Table 1.

Table 1 contains aerobic count data for filtrates taken at each of the times (in seconds) below using different techniques to release analytes from the source.

TABLE 1

| Sample No. | Source | Agitation Technique | Time 15 sec. | Time 30 sec. | Time 60 sec. | Time 120 sec. | Time 240 sec. |
|---|---|---|---|---|---|---|---|
| C1 | Ground Beef | STOMACHER ® | 16 | 168 | 171 | 172 | 127 |
| C2 | Ground Pork | STOMACHER ® | 21 | 147 | 161 | 173 | 168 |
| C3 | Spinach Leaves | STOMACHER ® | 13 | 216 | 238 | 247 | 223 |
| E1 | Ground Beef | Mechanical Shaker | 14 | 192 | 205 | 191 | 155 |
| E2 | Ground Beef | Vortex Mixer | 32 | 155 | 187 | 150 | 154 |
| E3 | Ground Pork | Vortex Mixer | 02 | 131 | 157 | 197 | 181 |
| E4 | Spinach Leaves | Mechanical Shaker | 28 | 375 | 335 | 280 | 249 |
| E5 | Spinach Leaves | Vortex Mixer | 26 | 25 | 302 | 339 | 267 |

The results of Table 1 show that the recovery of analytes using the sample preparation system of the present disclosure is comparable to that of the stomaching device. Preparation of the liquid compositions was greatly facilitated by the use of the sample preparation systems of the present disclosure in combination with mechanical shaking and vortex mixing.

The embodiments described and exemplified above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. Various features and aspects of the invention are set forth in the following claims.

What is claimed is:

1. A method for preparing samples to test for an analyte of interest, the method comprising:
   providing a liquid composition comprising a source and a diluent;
   providing a sample preparation system comprising a deformable freestanding liner, and a freestanding container that is more rigid than the deformable freestanding liner;
   positioning the liquid composition in a reservoir defined by the deformable freestanding liner;

positioning the deformable freestanding liner in the freestanding container;

removing a sample from the sample preparation system by applying pressure to the deformable freestanding liner; and analyzing the sample for the analyte of interest.

2. The method of claim 1, wherein the sample preparation system comprises a disposable portion comprising a lid coupled to the deformable freestanding liner, and further comprising removing the disposable portion of the sample preparation system from the freestanding container, and disposing of the disposable portion.

3. The method of claim 1, wherein the sample preparation system further comprises a lid, the method further comprising coupling the lid to at least one of the deformable freestanding liner and the freestanding container.

4. The method of claim 1, further comprising filtering the liquid composition to form a filtrate, wherein removing a sample from the sample preparation system includes removing at least a portion of at least one of the liquid composition and the filtrate, and wherein removing at least a portion of the filtrate occurs during the filtering step.

5. The method of claim 1, wherein the deformable freestanding liner includes a first sidewall and the freestanding container includes a second sidewall, and further comprising agitating the liquid composition, wherein agitating the liquid composition includes positioning an obstruction between the first sidewall and the second sidewall when the deformable freestanding liner is positioned in the freestanding container.

6. The method of claim 1, further comprising agitating the liquid composition.

7. The method of claim 1, wherein the freestanding container includes an aperture formed therein, and wherein applying pressure to the deformable freestanding liner includes applying pressure to the deformable freestanding liner via the aperture in the freestanding container.

8. The method of claim 1, wherein the deformable freestanding liner includes a base, wherein the freestanding container includes a base comprising an aperture defined therein, and wherein applying pressure to the deformable freestanding liner includes applying pressure to the base of the deformable freestanding liner via the aperture in the base of the freestanding container.

9. The method of claim 1, positioning the liquid composition in a reservoir defined by the deformable freestanding liner includes at least one of:

positioning the source comprising the diluent in the reservoir, adding the source and the diluent to the reservoir simultaneously, adding the source to the reservoir prior to adding the diluent to the reservoir, adding the diluent to the reservoir prior to adding the source to the reservoir, and combining the source and the diluent to form a liquid composition, and adding the liquid composition to the reservoir.

10. A sample preparation system comprising:

a deformable freestanding liner comprising a first reservoir;

a freestanding container comprising a second reservoir, the freestanding container being more rigid than the deformable freestanding liner, the second reservoir dimensioned to receive the deformable freestanding liner, the freestanding container including a base comprising an aperture formed therein through which the deformable freestanding liner can be accessed;

a liquid composition comprising a source and a diluent, the liquid composition positioned in the first reservoir; and a sampling port positioned in fluid communication with at least one of the first reservoir and the second reservoir, the sampling port configured to allow removal of a sample from the first reservoir.

11. The sample preparation system of claim 10, further comprising a filter positioned in fluid communication with at least one of the first reservoir and the second reservoir, the filter adapted to form a filtrate from the liquid composition, and wherein the sample includes at least a portion of at least one of the liquid composition and the filtrate.

12. The sample preparation system of claim 10, further comprising a lid, wherein the lid is adapted to be coupled to at least one of the deformable freestanding liner and the freestanding container.

13. The sample preparation system of claim 12, wherein the sample preparation system comprises a disposable portion comprising the lid coupled to the deformable freestanding liner.

14. The sample preparation system of claim 12, further comprising a filter in fluid communication with the reservoir, wherein the filter is substantially planar and coupled to an inner surface of the lid.

15. The sample preparation system of claim 10, wherein the analyte of interest includes at least one of a microorganism, a biomolecule, a chemical, a metal ion, a metal-ion-containing complex, and combinations thereof.

16. The sample preparation system of claim 10, wherein the source comprises the diluent.

17. The sample preparation system of claim 10, wherein the diluent includes at least one of a surfactant, a rheological agent, an antimicrobial neutralizer, a nutrient, a pH buffering agent, an enzyme, an indicator molecule, sterile water, an organic solvent, and a combination thereof.

18. The sample preparation system of claim 10, further comprising a filter coupled to the sampling port, the filter adapted to form a filtrate from the liquid composition, wherein the sample includes at least a portion of the filtrate.

19. The sample preparation system of claim 10, wherein the deformable freestanding liner comprises a relatively rigid base and a relatively deformable sidewall.

20. A method for preparing samples to test for an analyte of interest, the method comprising:

providing a liquid composition comprising a source and a diluent;

providing a sample preparation system comprising a deformable freestanding liner, and a freestanding container that is more rigid than the deformable freestanding liner, wherein the deformable freestanding liner includes a first sidewall and the freestanding container includes a second sidewall;

positioning the liquid composition in a reservoir defined by the deformable freestanding liner;

positioning the deformable freestanding liner in the freestanding container;

agitating the liquid composition, wherein agitating the liquid composition includes positioning an obstruction between the first sidewall and the second sidewall when the deformable freestanding liner is positioned in the freestanding container;

removing a sample from the sample preparation system; and analyzing the sample for the analyte of interest.

* * * * *

UNITED STATES PATENT AND TRADEMARK OFFICE
CERTIFICATE OF CORRECTION

| | | |
|---|---|---|
| PATENT NO. | : 8,272,255 B2 | |
| APPLICATION NO. | : 12/301592 | |
| DATED | : September 25, 2012 | |
| INVENTOR(S) | : Kurt J Halverson et al. | |

It is certified that error appears in the above-identified patent and that said Letters Patent is hereby corrected as shown below:

<u>Title Page 2, Column 2 (Foreign Patent Documents)</u>
Line 15, Delete "Wo 03/092573" and insert -- WO 03/092573 --, therefor.

<u>Title Page 2, Column 2 (Other Publications)</u>
Line 6, Delete ""Usefullness" and insert -- "Usefulness --, therefor.
Line 16-17, Delete "Bactheriological" and insert -- Bacteriological --, therefor.
Line 24, Delete "Fournal" and insert -- Journal --, therefor.

<u>Column 4</u>
Line 21, Delete "botulinun," and insert -- botulinum, --, therefor.

<u>Column 12</u>
Line 50, Delete "substate," and insert -- substrate, --, therefor.

<u>Column 16</u>
Line 49, Delete "Burell" and insert -- Burrell --, therefor.

Signed and Sealed this
Eighth Day of January, 2013

David J. Kappos
*Director of the United States Patent and Trademark Office*